United States Patent [19]

Cooke

[11] Patent Number: 5,579,781
[45] Date of Patent: Dec. 3, 1996

[54] WIRELESS TRANSMITTER FOR NEEDLE ELECTRODES AS USED IN ELECTROMYOGRAPHY

[76] Inventor: Thomas H. Cooke, 651 Strander Blvd., No. 100, Seattle, Wash. 98188

[21] Appl. No.: 322,777

[22] Filed: Oct. 13, 1994

[51] Int. Cl.⁶ .................................................. A61B 5/0488
[52] U.S. Cl. .............................. 128/733; 128/903; 607/60
[58] Field of Search .................................... 128/733, 734, 128/735, 903; 607/60; 364/413.05

[56] References Cited

U.S. PATENT DOCUMENTS

| | | | |
|---|---|---|---|
| 4,262,673 | 4/1981 | Kinney et al. | 607/37 |
| 4,791,933 | 12/1988 | Asai et al. . | |
| 4,793,353 | 12/1988 | Borkan . | |
| 4,819,860 | 4/1989 | Hargrove et al. . | |
| 5,161,533 | 11/1992 | Prass et al. | 128/733 |
| 5,168,874 | 12/1992 | Segalowitz . | |
| 5,212,476 | 5/1993 | Maloney . | |
| 5,233,999 | 8/1993 | Dellacoma et al. | 128/733 |
| 5,368,042 | 11/1994 | O'Neal et al. | 128/733 |
| 5,373,852 | 12/1994 | Harrison et al. | 128/733 |
| 5,443,065 | 8/1995 | Berghoff et al. | 128/639 |
| 5,452,719 | 9/1995 | Eisman et al. | 128/733 |

OTHER PUBLICATIONS

Kuck, A., Liebman, F. M., and Kussick, L. "A Miniature Transmitter for Telemetering Muscle Potentials", IEEE Transactions on Biomedical Electronics, vol. BME–10, No. 3, pp. 117–119, Jul. 1963.

Nielsen, J. F. and Wagner, G. "Implantable FM–Telemetry Transmitters for Registration of Biopotentials", Conference: International Symposium on Biotelemetry, Nijmegen, Netherlands, May 5–8, 1971, pp. 360–364.

Prochazka, V. J. Tate, K., Westerman, R. A., and Ziccone, S. P. "Remote monitoring of muscle length and EMG in unrestrained cats", Electroencephalography and Clinical Neurophysiology, vol. 37, No. 6, pp. 649–653, Dec. 1974.

Primary Examiner—Angela D. Sykes
Assistant Examiner—Eric F. Winakur
Attorney, Agent, or Firm—Graybeal Jackson Haley & Johnson

[57] ABSTRACT

A self-contained, battery powered, hand-held transmitter usable with mono or bipolar needle electrodes to sense electrochemical nerve impulses as transmitted through the nervous system and muscles of humans and animals. The hand-held transmitter is of miniaturized, generally rectangular form and comprises electronics developing and transmitting a VHF signal receivable by conventional FM receiver means. Being wireless, the transmitter avoids the possible signal distortions and restrictions of patient and physician movements which are inherent when using cable interconnections between electromyographic sensors and associated analytical equipment.

6 Claims, 3 Drawing Sheets

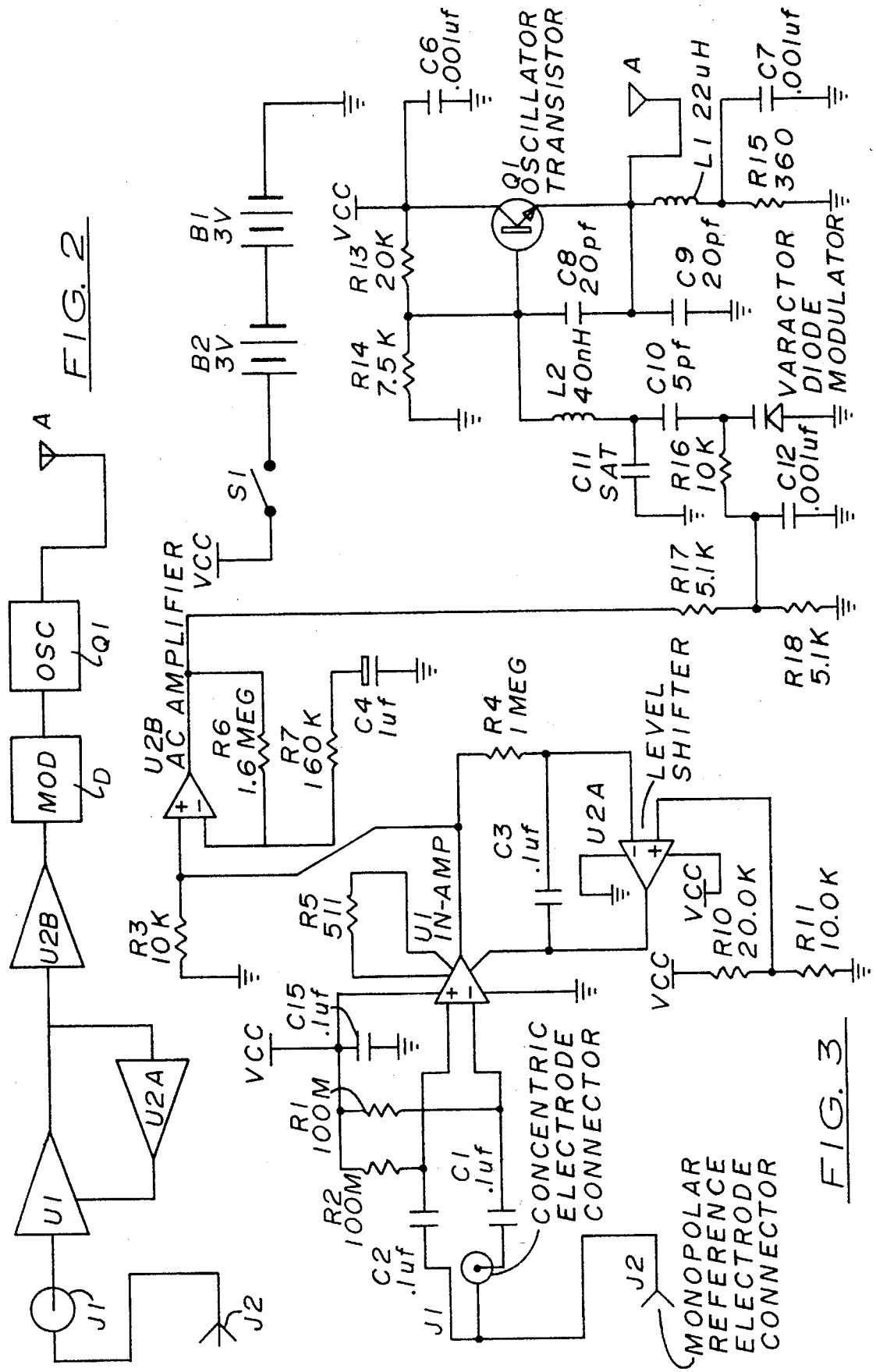

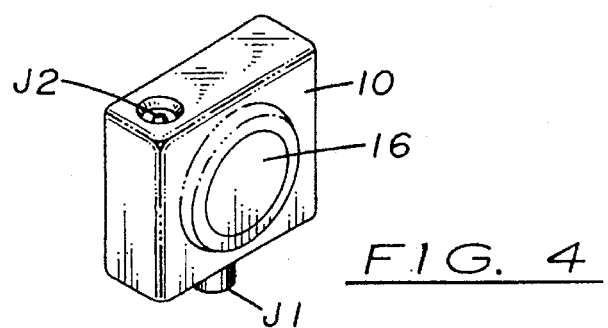
FIG. 4
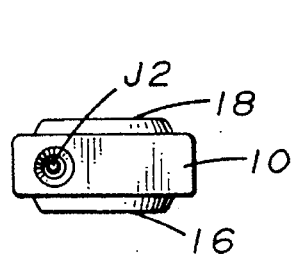
FIG. 5A
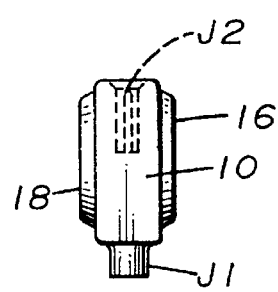
FIG. 5B
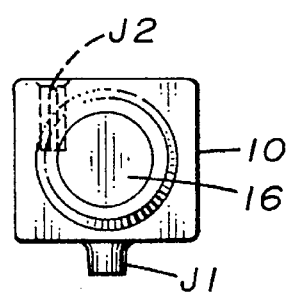
FIG. 5C
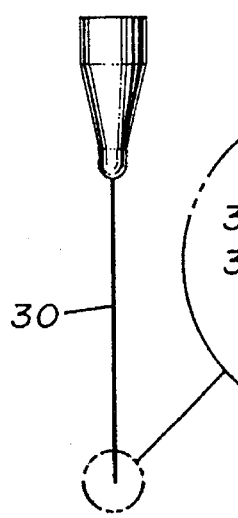
FIG. 6A
FIG. 6A-1
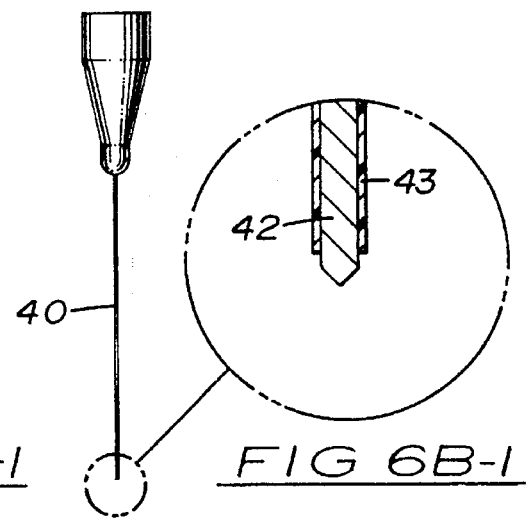
FIG. 6B
FIG 6B-1

WIRELESS TRANSMITTER FOR NEEDLE ELECTRODES AS USED IN ELECTROMYOGRAPHY

BACKGROUND OF THE INVENTION

The present invention relates to improved medical instrumentation usable in the field of electromyography (EMG), i.e. for the sensing, selective development and recordation of electrochemical nerve impulses as transmitted through the nervous systems and muscles of humans and animals. Specifically, the invention involves a wireless transmitter to which mono or bipolar medical electrodes are directly connectable and from which electrical signals are transmitted by radiant energy to remote but associated receiver and audio or visual display or recorder equipment.

DESCRIPTION OF THE PRIOR ART

It is well known that human and animal muscle k5 activities are controlled by nerve impulses transmitted electrochemically through the nervous system. Electrical signals related to muscle and nerve activity can be detected through use of medical electrodes applied to the surface of the skin or through electrodes which penetrate the skin, commonly known as needle electrodes. The electrical signals thus detected after suitable amplification can be displayed on an oscilloscope or recorded on a chart recorder or the like or may be applied to a speaker to provide audio representations of such signals. Since the electrical signals on the surface of the skin tend to represent a mixing of electrical signals over an undesirably large area, it is often preferable to employ subcutaneously applied needle electrodes to obtain signals from a particular location in the body, and also to obtain the electrical voltage level of the body in general as a reference voltage base. Concentric bipolar electrodes are used when the field of interest is more restricted. With concentric electrodes, the referenced area of the needle is separated by an insulated area from an active detection area on the same needle, and the active detection area often is typically quite small, 0.03 to 0.06 inch in length, for example.

Several problems have been encountered in use of prior art subcutaneous electrical signal sensing and amplification and display systems. The voltage amplitude of the signals detected by needle electrode sensors is very low and in a conventional prior art system the signal must be conveyed to signal amplifier and recording or display instrument by cable means, i.e. the overall system is a so-called "wired" system. Wire cables are subject to triboelectric phenomena whereby small electrode potentials are caused by physical movements of the signal carrying electrical cable. The triboelectric potentials can be of sufficient magnitude to mask or at least distort the desired electromyographic signals from the needle sensor. While the effect may be reduced by using cable that has been manufactured in such a way as to reduce triboelectric effects, the problem generally necessitates careful placement of the cables and attachment thereof to associated equipment, by means of tape for example, in order to minimize movement of the cables during medical procedures. This obviously can be inconvenient and can take up the time of the health care practitioner using the equipment.

It is also known that typical clinical environments often have a high level of electrical activity including the presence of 60 Hz signals and harmonics thereof from electrical wiring in the building or associated equipment. A human or animal body serves as an antenna for reception of these signals which are at frequencies within the range of frequencies of interest in electromyography. Amplifiers with high insulation from ground and shielded cables from the sensors are required in order to reduce the amount of pickup of unwanted 60 Hz and other interfering signals.

It is also a disadvantage of conventional electromyographic equipment, in which the sensor electrodes are wired to the associated amplification and display equipment that the wiring involved between the electrodes and the related equipment restricts the range of motion of the patient which may require the physician to forego certain movements of interest, and which can also impede the movement of the physician around the patient.

SUMMERY OF THE INVENTION

The present invention provides for users of electromyographic equipment a wireless, hand-held sensor and transmitter which is self-contained and self-powered, and which is usable with generally conventional FM radio receivers and conventional display and recording or audioamplification equipment. The transmitter suitably operates at a VHF frequency of about 250 MHz, and involves an antenna of about one inch size, as compared with a conventional cable innerconnection between a sensor and related equipment of about thirty inches. Sensors in the form of needle electrodes of conventional design per se, either monopolar or bipolar, are readily directly attachable to and removable from the transmitter.

The self-contained hand-held transmitter of the present invention is also usable with external reference electrodes if desired and also is provided with battery power and magnetic reed switch means for automatic power turn-on and turn-off as desired.

These and other features, advantages and unique characteristics of electromyographic needle transmitters according to the present invention will be apparent to those skilled in the art in the light of the following detailed description and accompanying drawings illustrating a preferred embodiment thereof.

DESCRIPTION OF THE DRAWINGS

FIG. 2 is a block diagram of the electrical circuit of the transmitter shown in FIG. 1.

FIG. 3 is a schematic of the electrical circuit of the transmitter shown in FIG. 1.

FIG. 4 is an isometric view of the transmitter of FIG. 1 in assembled form.

FIGS. 5A, 5B and 5C are respective top, side and front views of the transmitter shown in FIG. 1.

FIGS. 6A-1 and 6B-1 are respective bipolar (coaxial) and monopolar needle electrodes usable with the transmitter shown in FIGS. 1 and 5A–C.

DESCRIPTION OF THE EMBODIMENT

Figure 1:
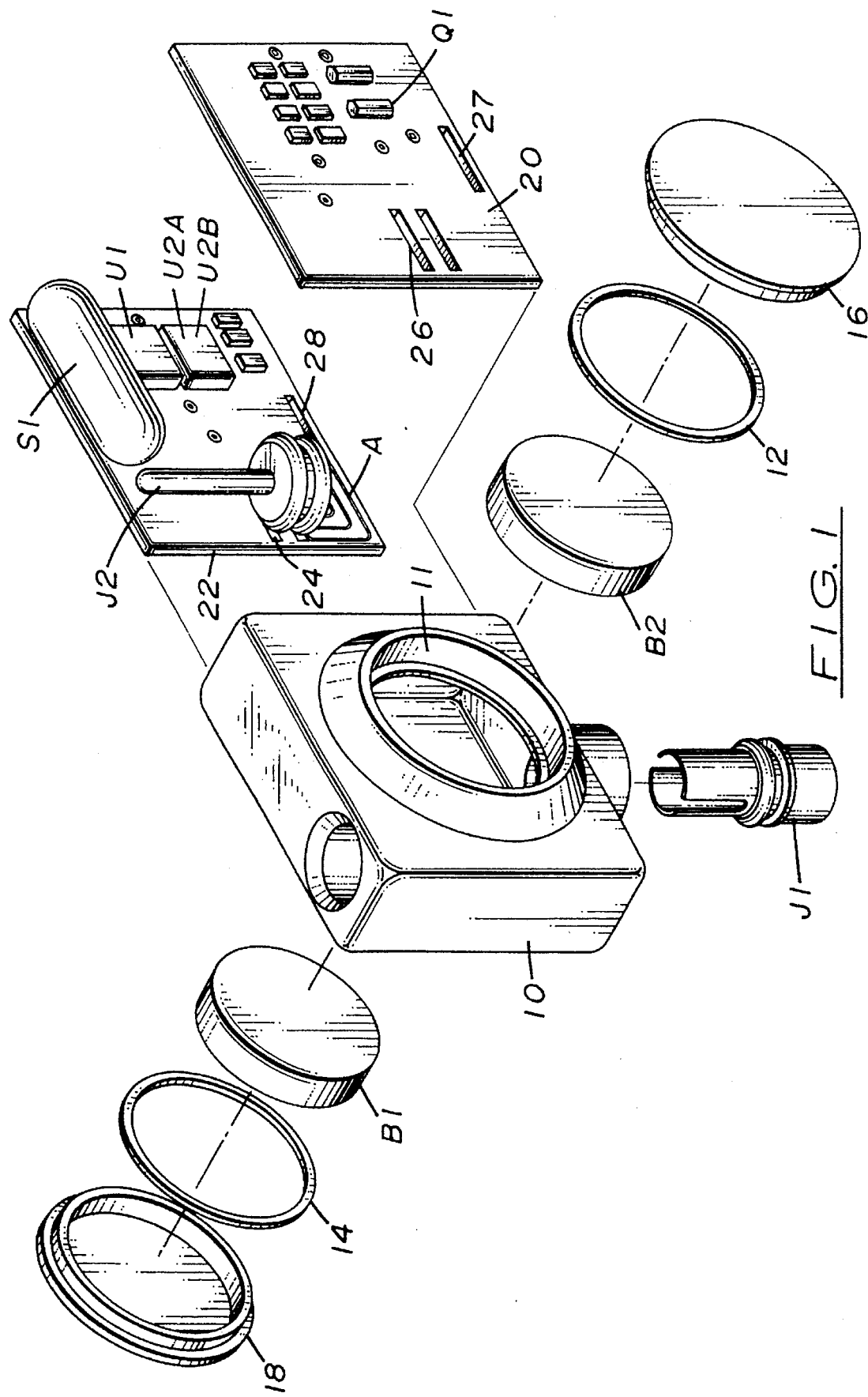
FIG. 1 is an exploded isometric view of a preferred embodiment of a needle electrode transmitter according to the present invention.

FIG. 1 is an exploded isometric view showing much of the details of an embodiment of a needle transmitter according to the present invention. With reference to it and the schematic showing in FIG. 3, the transmitter comprises a molded case 10 in which the major components of the transmitter are encapsulated, with the encapsulating plastic medium being not shown for clarity of other detail. Case 10 has in its bottom portion a mono and bipolar concentric electrode connector J1 and in its upper portion a monopolar reference electrode connector J2. The transmitter is battery powered by 3 volt lithium batteries B1 and B2 which are placeable and replaceable within front and rear recesses in the case 10 (the front such recess being indicated at 11) and held in place by respective seals 12, 14 and friction fitted retainer caps 16, 18. Within the case 10 and its encapsulating medium are front and rear printed circuit boards 20, 22, on which are mounted the transmitter's electrical circuitry including high gain instrumentation signal amplifier U1, A.C. amplifier U2A (for signal restoration), and A.C. amplifier U2B, modulator diode D1, power oscillator transistor Q1, antenna A, and the remainder of the circuit components shown in FIG. 3. Input connector J2 is held in place between the printed circuit boards 20, 22 by its circular ribs being retained in respective slots 24, 26 and connector J1 by slots 27 and 28 in the boards 20 and 22. Also arranged in the region between the printed circuit boards 20 and 22 is magnetic reed switch S1.

FIG. 2 illustrates in simplified block diagram form the general nature of the FM transmitter utilized in the present invention. The input or inputs from one or both of the needle electrodes connected to the monopolar or bipolar electrode connector J1 and the reference electrode connector J2 is applied as an input to the high gain instrumentation signals amplifier U1 and the output from it (suitably at an amplification factor of 100:1) passes to a.c. operational amplifier U2B to which is added the output from DC level shifter U2A. The output from amplifier U2B is then applied to modulator D1, a variable capacitance diode, then to oscillator stage Q1, the output from which is applied to the antenna A.

As shown in the schematic diagram presented at FIG. 3, the transmitter circuit is powered by batteries B1 and B2 coupled with an on-off switch S1, preferably in the form of a magnetic reed switch. FIG. 3 also shows schematically other component identities and circuit details. Further identifications of these typical components and details are as follows:

| | |
|---|---|
| U1 | transister INA 118_SM from Burr-Brown |
| U2 | transistor AMBTLC25L2_SM from Texas Instruments |
| D1 | Variable capacitance diode BBY40CT from ZETEK |
| Q1 | transistor BFS17 from ZETEK |
| B1 | 3 V lithium battery from Panasonic 7 |
| B2 | 3 V lithium battery from Panasonic |
| C1 | .1 uf |
| C2 | .1 uf |
| C3 | .1 uf |
| C4 | 1 uf |
| C6 | .001 uf |
| C7 | .001 uf |
| C8 | 20 pf |
| C9 | 20 pf |
| C10 | 5 pf |
| C11 | 10 pf for example |
| C12 | .001 uf |
| C15 | 1 uf |
| R1 | 100M ohms |
| R2 | 100M ohms |
| R4 | 1M ohms |

-continued

| | |
|---|---|
| R5 | 511 ohms |
| R6 | 1.6M ohms |
| R7 | 160k ohms |
| R10 | 20k ohms |
| R11 | 10k ohms |
| R13 | 20k ohms |
| R14 | 7.5k ohms |
| R15 | 360 ohms |
| R16 | 10k ohms |
| R17 | 5.1k for example |
| R18 | 5.1k for example |
| L1 | 22 uH |
| L2 | 40 uH |

The transmitter illustrated and described as the preferred embodiment transmits at a power output of about 1 milliwatt and is designed to be used in the same room as the associated FM receiver. FIG. 4 shows an isometric view of the assembled transmitter. Dimensionally, the transmitter case 10 measures about 1 inch along each side. FIGS. 5A, B and C show respective top, side and front views of the transmitter.

FIG. 6A illustrates a bipolar needle electrode 30 which is conventional per se and of a type connectable by friction fit to the connector J1. Its needle tip portion 32 includes a central conductor 34 and a concentric outer conductor 36 insulated from the central conductor 34 by insulation 38.

FIG. 6B shows a monopolar needle electrode 40, also conventional per se, in which the needle tip portion 42 is a conductor with the main portion of the needle shaft coated with an insulation material 43, such as Teflon.

As will be apparent, the rear view of the transmitter is substantially the same as the front view thereof in FIG. 5C, but with the indentation showing the top of the reference electrode connector reversely positioned from the showing thereof in FIG. 5C.

As will also be apparent, the connector J2 as shown is suitably a male recessed plug of a type for receiving a conventional sleeve type female jack to which a grounded or otherwise located electrode (not shown) for reference purposes is connectable.

Also not shown but self-evident and conventional per se is the association and use of the transmitter with a suitable storage holder or container having a magnetic component positioned to influence the magnetic reed switch S1 to maintain such in open position when the transmitter is not in use and stored in the holder or container.

In general, the transmitter consists of a high gain instrumentation amplifier which is sensitive to a very low amplitude signal level from a monopolar or concentric needle electromyographic (EMG) voltage sensor. The signal, suitably amplified, and at an appropriate DC level, is applied to a voltage variable capacitance diode (varicap) which is a part of a tuned circuit consisting of the varicap, a capacitor and an inductor. Changes in the voltage at the varicap diode causes a change in the resonant frequency of the tuned circuit. The tuned circuit is a part of an oscillator with a natural frequency, suitably, of about 250 MHz. In this manner the frequency of the oscillator is modulated with the analog signal which corresponds to the electromyographic signal sensed by the needle sensor. A very short antenna on the order of one inch long is adequate to achieve sufficient radiated radio frequency energy to allow reception of the signal by an FM telemetry receiver. The receiver itself can be of generaly conventional design in which the received signals are amplified by a tuned low noise amplifier and the signal is then mixed at the output of a tunable oscillator operating at a suitable frequency of approximately 260 Mhz. The output of the mixer is passed through a filter with a center frequency of 10.7 Mhz and a bandwidth of approximately 110 KHz. The intermediate frequency signal output, suitably centered at 10.7 Mhz, the standard IF frequency in FM receivers, will vary in frequency in accordance with the EMF signal. This IF signal is then amplified and applied to a conventional FM demodulator which converts the frequency variations to voltage variations which reproduce the EMG signal generated at the sensor.

In order to meet size, cost and power restraints, the transmitter is necessarily simple, with the frequency of the transmission being controlled solely by the capacitance and inductance of the components of the oscillator tuned circuit. Such a simple oscillator is subject to frequency drift as the battery voltage changes, as components age and as oscillator components change in value with change in ambient temperature. In order to compensate for this frequency drift, the receiver should include automatic frequency control circuitry with selectable gain, circuits for which are known per se. At the time the transmitter is first installed, the receiver is to be tuned to the correct frequency with the transmitter on and close to the receiver. This can readily be done while listening to the characteristic EMG signal sounds on the receiver's audio output, e.g. its speaker. The receiver tuning is done with very low AFC gain so that the manual tuning is nearly uneffected by signals which are detected while searching for the desired signal. The desired signal can be readily identified by turning the transmitter off and on repeatedly while monitoring the received signals. When the real signal has been selected, the user can then select high AFC gain, which then can effectively lock the receiver on the received signal.

Also evident from the foregoing disclosure are various modifications which may be made to the transmitter and its components. Manually operated switch means for the transmitter power, such as a simple toggle or push button on-off switch means can be employed in lieu of the magnetic reed switch S1. Connector J2 can be omitted if desired. Component arrangements and other micro-chip circuitry can be utilized instead of the particular printed circuit board means shown and discussed. The transmitter can also be designed to be tunable in frequency although the additional circuitry which would be required is considered to be not essential to the underlying concept of the invention, that of a simple reliable hand-held wireless transmitter for use with needle electrodes in a clinical environment. Various further modifications and adaptations will occur to those skilled in the art to which the invention is addressed, within the scope of the following claims.

What is claimed is:

1. A self-contained, battery powered, hand-held, wireless transmitter usable with a disposable mono or bipolar needle electrode to sense electrochemical nerve impulses as transmitted through the nervous system and muscles of humans and animals, said transmitter comprising a generally rectangular molded plastic case with integrally formed top, bottom, side, front and rear walls, printed circuit board means arranged between and extending parallel to said front and rear walls of said case and engaging said sides thereof, electrical circuit components and circuitry on said printed circuit board means including a high gain instrumentation signal amplifier, a signal level shifter stage, an AC amplifier, a modulator diode, a power oscillator transistor, and an antenna, said electrical circuit components and circuitry also including an input connector jack extending through and below said bottom wall of said case for frictional and electrical interconnection with a needle electrode, said transmitter also comprising battery receptor recesses in said front and rear walls of said case in which are placeable batteries for powering said electrical circuit components and circuitry, and an encapsulating medium filling the interior of said case defined by said top, bottom, side, front and rear walls thereof and encapsulating said printed circuit board means and said electric circuit components circuitry thereon.

2. The transmitter of claim 1, further comprising a second needle electrode connector jack arranged and extending through the said top wall of said case for connection to a reference needle electrode.

3. The transmitter of claim 1, wherein said printed circuit board means comprises two printed circuit boards in parallel arrangement with respect to each other and with respect to said front and rear walls of said case.

4. The transmitter of claim 1, in combination with a storage holder therefor, said transmitter comprising a transmitter power circuit and a magnetic reed switch in said transmitter power circuit, and said storage holder comprising a magnetic component positioned to influence said magnetic reed switch in a manner maintaining such in open circuit condition when said transmitter is not in use and stored in said holder.

5. The transmitter of claim 1, wherein the said transmitter generates radiant energy at a carrier frequency in the VHF range which is receivable by a conventional FM receiver.

6. The transmitter of claim 1, wherein said front and rear walls of said case are about one inch in height and one inch in width.

* * * * *